United States Patent

Gero et al.

Patent Number: 4,716,226
Date of Patent: Dec. 29, 1987

[54] OPTICALLY ACTIVE 4-CARBALKOXY-2-AZETIDINONES

[75] Inventors: Stéphane Gero, Les Ulis; Jeanine Cleophax, Palaiseau; Alice Gateau-Olesker, Gif-Sur-Yvette, all of France

[73] Assignee: Roussel Uclaf, Paris, France

[21] Appl. No.: 791,774

[22] Filed: Oct. 28, 1985

[30] Foreign Application Priority Data

Nov. 2, 1984 [FR] France ................ 84 16759

[51] Int. Cl.$^4$ .............. C07D 205/08; C07B 41/04; C07B 41/02; C07B 53/00
[52] U.S. Cl. .............. 540/200; 540/364; 540/355; 560/180; 560/170; 560/150; 564/158; 564/160
[58] Field of Search ...................... 540/200

[56] References Cited

PUBLICATIONS

McOmie, Protective Groups in Organic Chemistry, pp. 96–97, (1973).
DeMarinis, Tet. Letters 23, 731–4, (1982).

*Primary Examiner*—Mark L. Berch
*Attorney, Agent, or Firm*—Bierman & Muserlian

[57] ABSTRACT

Novel 2-azetidinones of the formula

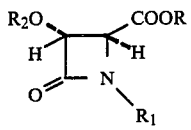

wherein R is alkyl of 1 to 4 carbon atoms, $R_1$ is selected from the group consisting of hydrogen, —OH, protected hydroxy and —OCH$_2$—COOR', R' is selected from the group consisting of hydrogen and alkyl of 1 to 4 carbon atoms and $R_2$ is selected from the group consisting of alkyl of 1 to 4 carbon atoms and hydroxyl protective group and a novel process and novel intermediates for their preparation and a process for the preparation of compounds of the formula

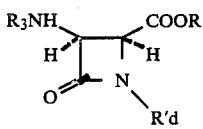

wherein R has the above definition, R'd is selected from the group consisting of hydrogen, —OH and protected hydroxyl and $R_3$ is selected from the group consisting of hydrogen and $R_3'$, $R_3'$ is amino protective group which are useful intermediates.

3 Claims, No Drawings

OPTICALLY ACTIVE 4-CARBALKOXY-2-AZETIDINONES

OBJECTS OF THE INVENTION

It is an object of the invention to provide the novel compounds of formula I and a process and novel intermediates for their preparation.

It is another object of the invention to provide a novel process for the preparation of compounds of formula VII starting from the compounds of formula I.

These and other objects and advantages of the invention will become obvious from the following detailed description.

THE INVENTION

The novel compounds of the invention are 2-azetidinones of the formula

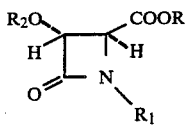

wherein R is alkyl of 1 to 4 carbon atoms, $R_1$ is selected from the group consisting of hydrogen, —OH, protected hydroxy and —OCH$_2$—COOR', R' is selected from the group consisting of hydrogen and alkyl of 1 to 4 carbon atoms and $R_2$ is selected from the group consisting of alkyl of 1 to 4 carbon atoms and hydroxyl protective group.

Among the preferred R, $R_2$ and R' when they are alkyl are methyl, ethyl, propyl, isopropyl, butyl and tertiary butyl. R and R' are more preferably methyl or ethyl.

The protective groups of the hydroxyl which $R_1$ can include or $R_2$ can be are chosen from among the usual known groups, in particular in the chemistry of the cephalosporines. In particular, there can be cited the acetyl, benzyl, trityl, benzhydryl, 4-methoxybenzyl, tetrahydropyrannyl, tert-butoxycarbonyl, $\beta\beta\beta$-trichloroethoxycarbonyl, benzyloxycarbonyl and ethoxycarbonyl.

Among the values of $R_1$ it is preferably benzyloxy and $R_2$ is preferably benzyl or methyl.

The novel process of the invention for the preparation of compounds of formula I comprises reacting a compound of the formula

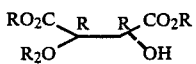

wherein R and $R_2$ have the above definitions with a mono-saponifying agent to obtain a compound of the formula

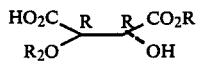

reacting the latter with a hydroxylamine derivative of the formula $R_1'$—O—NH$_2$, wherein $R_1'$ is a protective group of hydroxyl or CH$_2$—CO$_2$—R' and R' has the above definition to obtain a compound of the formula

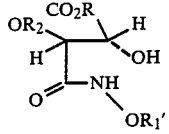

reacting the latter with a cyclizing agent to obtain a compound of the formula

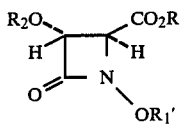

wherein $R_1'$, R and $R_2$ have the above definitions which is a compound of formula I wherein $R_1'$ is a protected hydroxyl or —OCH$_2$—CO$_2$—R', which product, when $R_1'$ is a protective group, is submitted, if desired, to a selective deprotection reaction to obtain a product of the formula

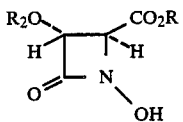

wherein R and $R_2$ have the above definition and is a compound of formula I in which $R_1$ is an unprotected hydroxyl, which product is reacted, if desired, with a reducing agent to obtain a compound of the formula

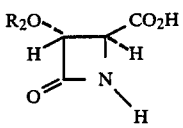

wherein R and $R_2$ have the above definitions and corresponds to a compound of formula I in which $R_1$ is hydrogen.

The mono-saponifying agent which is preferably reacted with the compound of formula II can be a mineral base such as an alkali metal carbonate, preferably potassium carbonate. The reaction is preferably effected in the presence of an excess of mineral base and in an aqueous organic solution such as an alcohol-water mixture or preferably a dioxane-water mixture. An esterase of vegetable or animal origin can also be used. For example, pork liver esterase can be used and the reaction is then carried out in a buffered medium, for example, in a phosphate buffer.

The reaction of the hydroxylamine derivative of the formula $R_1'ONH_2$ and the product of formula III can be carried out at ambient temperature using a salt of the hydroxylamine derivative such as the hydrochloride. The reaction can then be carried out in water or in a water-organic solvent mixture and is done in the presence, for example, of a carbodiimide, such as dicyclohexylcarbodiimide or, if it is done in an aqueous medium, in the presence of a soluble carbodiimide, such as 1-ethyl-3,3-dimethylaminopropylcarbodiimide hydrochloride. The solvent, in the presence of which the reaction can be done, is for example, tetrahydrofuran.

The cyclization of the products of formula IV into products of formula Ia can be effected by the intermediary of a sulfonic acid derivative of the hydroxyl and can be done, for example, by means of a sulfonic acid halide such as p-toluenesulfonyl chloride or methylsulfonyl chloride in the presence of a hydrohalic acid captor such as an amino base. The operation can also be done in a solvent such as pyridine or a mixture of pyridine with an organic solvent such as methylene chloride. The sulfonyl derivative thus obtained can be treated with a base such as an alkali metal carbonate, for example, potassium carbonate, to obtain the expected product of formula Ia. The cyclization reaction itself can be carried out in an organic solvent such as acetone. The cyclization of the products of formula IV can also be carried out in the presence of triphenylphosphine and diethylazodicarboxylate in an organic solvent, such as tetrahydrofuran.

The selective cleavage of $R_1'$ when the latter, in the products of formula Ia, is a protective group of the hydroxyl, is carried out by known methods. When $R_1'$ is a radical cleavable by hydrogenolysis such as the benzyl radical, the cleavage is carried out with hydrogen in the presence of a catalyst such as palladium on carbon.

The reducing agent to which products of formula Ib are possibly submitted is selected from the usual reagents, for example, titanium chloride.

Certain of the reactions of the process as indicated above, give rise to the formation of by-products which can generally be eliminated by known purification method, particularly chromatography. Such methods are described further on in the experimental part.

Particularly the reaction of the hydroxylamine derivative of the formula $R_1'$—$ONH_2$ with the compound of formula III give rise, as well as to the sought product of formula IV, also to by-products of the formulae

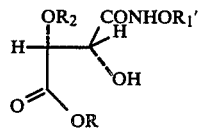

and

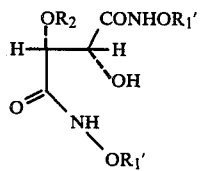

The by-products of formula IV can generally be easily eliminated by precipitation while the products of formula IV' can easily be eliminated by the usual methods during the later stage of the cyclization.

A preferred mode of the present invention is the said process in which the compound of formula II has $R_2$ as benzyl or methyl and the hydroxylamine derivative $R_1'ONH_2$ of formula III is 0-benzylhydroxylamine.

According to a preferred method of carrying out the process of the invention: (a) The mono-saponifying agent which reacts with the compound of formula II is either potassium carbonate or an esterase of animal origin. (b) The cyclizing agent reacting with the compound of formula IV is a derivative of a sulfonic acid which leads to the compound of the formula

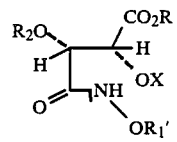

wherein X is tosyl

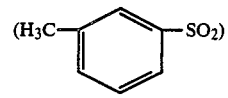

or mesyl ($CH_3$—$SO_2$) which product is cyclized in the presence of a base to give the product of formula Ia and (c) The cyclizing agent is a mixture of triphenyl phosphine and a dialkyl azodicarboxylate.

A further object of the invention is to provide a process for the preparation of the compounds of formula II wherein $R_2$ is alkyl of 1 to 4 carbon atoms by reacting a diester of tartaric acid of the formula

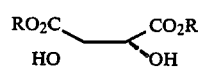

wherein R has the above definition with a diazoalkane in the presence of tin chloride. In a preferred method of carrying out this process, the product of formula V is complexed with tin chloride before alkylation in an organic solvent such as acetonitrile. The alkylation reaction with a diazoalkane, preferably diazomethane, is carried out under the usual conditions, for example, in an organic solvent such an ethyl ether.

A process of the invention for the preparation of the compounds of formula II wherein $R_2$ is a protective group of hydroxyl comprises reacting a diester of tartaric acid of formula V with a reactive derivative of the protective group in the presence of sodium hexamethyldisilazide. The reaction can be carried out in an organic solvent or in a mixture of organic solvents such as tetrahydrofuran and toluene.

A process of the invention for the preparation of compounds of formula II wherein $R_2$ is benzyl comprises reacting a compound of the formula

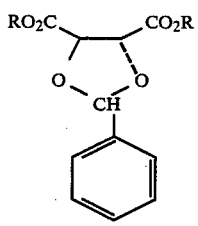

with a reducing agent which is preferably an alkali metal hydride or borohydride. Sodium cyanoborohydride is preferred and the reaction is effected in an organic solvent such as acetonitrile.

Another aspect of the invention is a process for the preparation of a compound of the formula

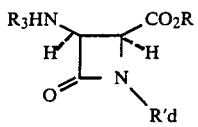 VII wherein R'd is selected from the group consisting of hydrogen, —OH and protected hydroxyl, R has the above definition and $R_3$ is hydrogen or $R_3'$ and $R_3'$ is an amino protective group comprising subjecting a compound of the formula

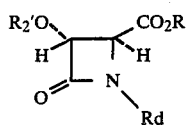 Id wherein R has the above definition, $R_2'$ is a hydroxyl protective group and Rd is hydrogen or a protected hydroxyl to a selective deprotection reaction to obtain a compound of the formula

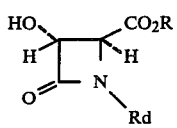 VIII wherein R and Rd have the above definition, reacting the latter with a sulfonic acid derivative of the formula

wherein $R_4$ is a sulfonic acid residue to obtain a compound of the formula

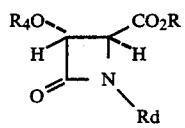 IX wherein R, Rd and $R_4$ have the above definitions, reacting the latter with an alkali metal azide to obtain a compound of the formula

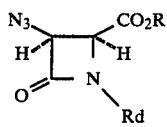 X wherein R and Rd have the above definitions, reacting the latter with a hydrogenation agent to obtain a compound of the formula

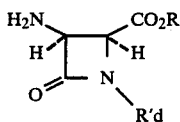 VIIa wherein R and R'd have the above definitions and optionally reacting the latter with a reagent capable of introducing a protector group of an amino to obtain a product of the formula

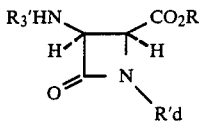 VIIb wherein R, R'd and $R_3'$ have the above definitions, subjecting the compounds of formulae VIIa and VIIb, if desired, when R'd is a protected hydroxyl, to a selective deprotection reaction to obtain a compound of the formula

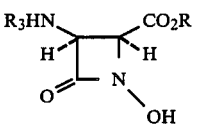 VIIc wherein R and $R_3$ have the above definitions and if desired, reacting the latter with a reducing agent to obtain a compound of the formula

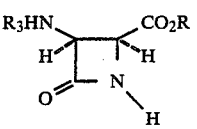 VIId wherein R and $R_3$ have the above definitions.

The protective groups of the hydroxyl which Rd can include can be chosen from the known groups cited above for $R_1$ and $R_2$. The invention is particularly characterized in that at the start a compound of formula Id is used in which Rd is a protected hydroxyl and particularly an acyloxy group.

In a preferred method of carrying out the use according to the invention: The selective deblocking reaction to which the compound of formula Id is submitted is carried out by the usual methods. When the protective group of the hydroxyl is cleavable by hydrogenolysis such as benzyl, the cleavage is carried out with hydrogen in the presence of a catalyst such as palladium on carbon. Among the sulfonic acid derivatives of the formula $R_4$—OH, there can be cited those wherein $R_4$ is methylsulfonyl ($CH_3$—$SO_2$), p-toluene sulfonyl ($H_3C$—Ph—$SO_2$) or trifluoromethylsulfonyl ($F_3C$—$SO_2$). The sulfonic acid derivative which reacts with the compound of formula VIII is preferably a derivative of trifluoromethyl sulfonic acid. The anhydride or the acid chloride is used, more especially the anhydride, and the reaction is effected in the presence of an amine base such as pyridine in an organic solvent such as methylene chloride.

The alkali metal azide is preferably sodium azide and the reaction is done in an organic solvent such as benzene. The reduction of the azide of formula X to an amino derivative is carried out by the usual methods, for example by catalytic hydrogenation. The possible protection of the amino is achieved by reagents known in the chemistry of peptides and β-lactams. A list of such substituents can for example be found in French Pat. No. 2,495,613 and the carbobenzyloxy radical is preferably used.

The reagent able to introduce this group is for example, benzyl chloroformate in the presence of a base such as sodium bicarbonate.

The preparation of compounds of formulae VIIc and VIId starting with compounds of the formulae VIIa and VIIb is carried out by a method which is identical to that indicated for the preparation of compounds of formulae Ib and Ic starting with compounds of formula Ia.

The novel intermediate of the invention are compounds of the formula

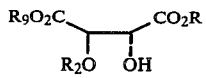

wherein R and $R_2$ have the above definitions and $R_9$ is hydrogen or is R.

Among the preferred compounds of formula I are those wherein $R_2$ is benzyl, those wherein $R_1$ is hydrogen and those wherein R is methyl or ethyl.

The compounds of the formula I are intermediates useful in the synthesis of $\beta$-lactams which are anti-biotics. For example, compounds of formula Ic wherein $R_2$ is a protective group of the hydroxyl can be converted into $\beta$-lactams including, at position 3, an amino group. Examples of such reactions are given, for example, in publications such as Liebigs Annalen der Chemie (1974) p. 369; or J.A.C.S. Vol. 105, p. 7,345 (1983).

The products thus obtained can be acylated and sulfonylated following known processes in literature to obtain compounds such as those described in French Pat. No. 2,495,613. The compounds wherein $R_1$ is —$OCH_2$—$CO_2R$ can be used to prepare by known methods the compounds of oxamazine type as described in Tet. let. Vol. 25 No. 32 p. 3,425.

In the following examples there are described several preferred embodiments to illustrate the invention. However, it is to be understood that the invention is not intended to be limited to the specific embodiments.

EXAMPLE 1

Methyl(2S-trans)-1-phenylmethoxy-3-methoxy-4-oxo-2-azetidine carboxylate

Step A

Methyl[2R-(R*,R*)]-2-hydroxy-4-oxo-3-methoxy-4-[(phenylmethoxy)-amino]-butanoate 235 mg of dimethyl[R-(R*,R*)]-2-hydroxy-3-methoxy-butanedioate and 336 mg of potassium carbonate (2.44 mM) were dissolved in 6 ml of a 1/1 dioxane/$H_2O$ mixture, and the solution was stirred at ambient temperature for 5 hours. The reaction mixture was treated with Amberlite IRN 77 (H+), filtered and evaporated to dryness. The 190 mg of crude product and 182 mg, (1.1 equiv.) of 0-benzylhydroxylamine hydrochloride were dissolved in 10 ml of water and a solution of 345 mg of ethyl-1-dimethylaminopropyl-3,3-carbodiimide (1.5 equiv) in 5 ml of water was added while maintaining the pH at 4.5 by the addition of a 1N hydrochloric acid solution. After half an hour, 35 mg (10%) of [2R-R*,R*)]-2-hydroxy-3-methoxy-N,N'-bis-(phenylmethoxy)-butanediamide precipitate were isolated by filtration and extraction of the aqueous phase with $CH_2Cl_2$ yielded 300 mg of product which was purified by chromatograhy over silica gel and elution with a ACOEt/HEXANE (8/2) mixture to obtain 200 mg of a mixture of methyl[2R-(R*,R*)]-2-hydroxy-4-oxo-3-methoxy-4-[(phenylmethoxy)-amino]-butanoate and methyl[2R-(R*,R*)]-2-methoxy-4-oxo-3-hydroxy-4-[(phenylmethoxy)-amino]-butanoate in a ratio of about 6.5/3.5 according to the NMR $^1H$.

NMR $^1H$ (60 MHz): 3.3 ppm and 3.4 (s, 3H, 6.5/3.5); 3.6 and 3.8 (s, 3H), 4.15 (s widened, 1H); 4.3–4.5 (m, 2H); 4.8 (s widened, 2H); 7.2 (s 5H); 9.31 (m, 1H).

Step B

Methyl(2S-trans)-1-phenylmethoxy-3-methoxy-4-oxo-2-azetidine-carboxylate

The mixture of Step A was dissolved in 5 ml of a 1/1 pyridine/$CH_2Cl_2$ mixture and at $-10°$ C., 0.1 ml of mesyl chloride was added and the reaction was stirred for 4 hours. After extraction with $CH_2Cl_2$, the crude product was dissolved in acetone and added to a suspension of 200 mg. (1.5 equiv.) of potassium carbonate in acetone at 60° C. and after one hour of stirring, filtration and chromatography (eluent: ACOEt/hexane 1/1), 40 mg of methy l(2S-trans)-1-phenylmethoxy-3-methoxy-4-oxo-2-azetidine-carboxylate (Yield=22%) with a specific rotation of $[\alpha]_D^{25} = +37°$ (c=0.54% in $CHCl_3$). were obtained.

Analysis: $C_{13}H_{15}O_5N$: Calculated: %C 58.85 %N 5.70 %N 5.28. Found: 58.83 5.74 5.53.

NMR $^1H$ (200 MHz): 3.43 ppm (s, 3H); 3.76 (s, 3H); 4.04 (d, 1H, $J_{3,4}=1.5$ Hz); 4.40 (d. 1H, $J_{3,4}=1.5$ Hz); 5.08 (q, 2H); 7.34 (s, 5H).

EXAMPLE 2

Methyl(2S-trans)-1,3-bis-(phenylmethoxy)-4-oxo-2-azetidine-carboxylate

Step A

Methyl[2R-(R*,R*)]-2-hydroxy-4-oxo-3-phenylmethoxy-4-[(phenylmethoxy)-amino]-butanoate 470 mg of dimethyl[R-(R*,R*)]-2-hydroxy-3-phenylmethoxy butanedioate were reacted as in Step A of Example 1 with 600 mg of potassium carbonate. The crude residue was treated directly with 840 mg of 0-benzyl hydroxylamine hydrochloride and 1 g of ethyl-1-dimethylaminopropyl-3,3-carbodiimide hydrochloride. After chromatography over silica gel and elution with ACOEt/hexane (8:2), 50 mg of [2R-(R*,R*)]-2-hydroxy-N,N'-3-tris(phenylmethoxy)butanediamide and 400 mg of a mixture of methyl[2R-(R*,R*)]-2-hydroxy-4-oxo-3-phenylmethoxy-4-[(phenylmethoxy)-amino]-butanoate and methyl[2R-(R*,R*)]-3-hydroxy-4-oxo-2-phenylmethoxy-4-[(phenylmethoxy)-amino]-butanoate in a ratio of about 6/1 according to the NMR were obtained.

Analysis: $C_{19}H_{21}O_6N$: Calculated: %C 63.49 %H 5.89 %N 3.89. Found: 63.23 6.05 3.91.

NMR $^1H$ (60 MHz) 3.58 ppm (s, 3H); 3.7–4.6 (strong, 5H); 4.85 (s); 7.11 (m, 1OH). 8.98 and 9.78 (s widened, 1H% 6/1).

IR: $\nu CO_2R=1730$, $\nu CONHOR=1670$.

Step $B_1$

Methyl(2S-trans)-1,3-bis-(phenylmethoxy)-4-oxo-2-azetidino carboxylate 150 mg of the mixture of Step A was reacted with 2 equiv. (0.6 ml) of mesyl chloride in a pyridine-methylene chloride mixture (1/1) at $-10°$ C. for 2 hours. After extraction and evaporation, the residue was dissolved in acetone and added to a suspension of 1.5 equiv. (83 mg) of potassium carbonate in acetone at 60° C. At the end of 20 minutes, after filtration and evaporating the solvent, the crude product was chromatographed over silica gel (eluent: ACOEt/hexane, 1/1) to obtain 27 mg of methyl(2S-trans)-1,3-bis-(phenylmethoxy)-4-oxo-2-azetidino carboxylate (Yield=20%) with a specific rotation of $[\alpha]_D^{25} = +51°$ (c=0.69%) in CHCl$_3$).

Analysis: C$_{19}$H$_{19}$O$_5$N: Calculated: %C 66.84 %H 5.61 %N 4.10. Found: 66.82 5.72 3.96.

IR: $\gamma$CO$_2$Me=1740, lactam=1790.

NMR $^1$H (400 MHz, CDCl$_3$): 3.75 ppm (s, 3H); 4.04 (d, 1H, J$_{3,4}$=1.5 Hz); 4.54 (d, 1H, J$_{3,4}$=1.5 Hz); 4.67 (q, 2H); 5.07 (q. 2H); 7.38 (m, 10H).

Step B$_2$ methyl(2S-trans)-1,3-bis-(phenylmethoxy)-4-oxo-2-azetidino-carboxylate 300 mg of the mixture of Step A and 435 mg of triphenylphosphine were dissolved in 5 ml of tetrahydrofuran under argon and 0.26 ml (2 equiv.) of diethylazodicarboxylate were added by syringe. After 2 hours, the solution was evaporated and the residue was chromatographed (eluent: ACOEt/hexane, 1/1) to obtain 50 mg of the starting hydroxamates (17%) and 96 mg of methyl(2S-trans)1,3-bis-(phenylmethoxy)-4-oxo-2-azetidino carboxylate identical to that obtained at Step B$_1$.

Step B$_3'$ methyl[2R-(R*,R*)]-2-[(4-methylphenylsulfonyl)-oxy]-4-oxo-3-(phenylmethoxy-4-[(phenylmethoxy)-amino]-butanoate 440 mg of the mixture of Step A were dissolved in 3 ml of pyridine and 2 ml of CH$_2$Cl$_2$ at −10° C. and 2.5 equiv. of tosyl chloride were added (580 mg). The mixture was stirred for 2 days at −10° C. and after extraction and chromatography (ACOEt/hexane, 2/8), 90 mg of the starting product, 420 mg of methyl[2R-(R*,R*)]-2[(4-methylphenylsulfonyl)-oxy]-4-oxo-3-(phenylmethoxy-4-[(phenylmethoxy)-amino]-butanoate and methyl-[2R-(R*,R*,R)]-3-[(3-[(4-methylphenylsulfonyl)-oxy]-4-oxo-2-(phenyl-methoxy)-4-[(phenylmethoxy)-amino]-butanoate were obtained.

NMR $^1$H (60 MHz): 2.3 ppm (s, 3H); 3.55 (s, 3H); 4.3 (s, 2H); 4.4 (d, 1H, J$_{2,3}$=2 Hz); 4.6 (s, 2H); 5.25 (d, 1H, J$_{2,3}$=2 Hz); 7–7.25 (7H); 7.6 (d, 2H); 8.7 (m. 1H).

Step B$_3''$

Methyl(2S-trans)-1,3-bis-(phenylmethoxy)-4-oxo-2-azetidinocarboxylate 57 mg of the compound of Step B$_3'$ were dissolved in 3 ml of acetone and 46 mg of potassium carbonate in acetone at 60° C. were added. After 1 hour of stirring, the reaction mixture was filtered and evaporated to obtain 28 mg quantitatively of methyl(2S-trans)-1,3-bis-(phenylmethoxy)-4-oxo-2-azetidino-carboxylate identical to the product previously obtained.

EXAMPLE 3

Ethyl-(2-S, trans)-1-phenylmethoxy-3-methoxy-4-oxo-2-azetidine-carboxylate

Step A

Ethyl[2R-(R*,R*)]-2-hydroxy-4-oxo-3-methoxy-4-[(phenylmethoxy)-amino]-butanoate 610 mg of diethyl[R-(R*,R*)]-2-hydroxy-3-methoxy-butanedioate and 930 mg of potassium carbonate were reacted by procedure of Step A of Example 1 and the crude product obtained was treated with 1.34 g of 0-benzylhydroxylamine hydrochloride and 1.6 g of ethyl-1-dimethylaminopropyl-3,3-carbodiimide hydrochloride. After half an hour of reaction, the mixture was extracted and the residue was chromatographed over silica (ethyl acetate-hexane 8:2) to obtain 40 mg of [2R-(R*,R*)]-2-hydroxy-3-methoxy-N,N'-bis-(phenylmethoxy)butanediamide as well as 460 mg of a mixture of ethyl[2R-(R*,R*)]-2-hydroxy-4-oxo-3-methoxy-4-(phenylmethoxy)-amino]-butanoate and ethyl[2R-(R*,R*)]-2-methoxy-4-oxo-3-hydroxy-4-[(phenylmethoxy)-amino]-butanoate in a ratio of 7:1.

Analysis: C$_{14}$H$_{19}$O$_6$N: Calculated: %C 56.55 %H 6.44 %N 4.71. Found: 56.45 6.32 4.51.

NMR $^1$H (60 MHz): 1.25 ppm(t, 3H); 2.8 (s, 1H); 3.22 (s) and 3.35 (s, 3H); 4–4.85 (6H); 7.18 (s, 5H); 8.75 and 9.25 (7/1=1H).

Step B' ethyl[2R-(R*,R*)]2-[4-(methylphenylsulfonyl)-oxy]-4-oxo-3-methoxy-4-[(phenylmethoxy)-amino]-butanoate 475 mg of a mixture of ethyl[2-(R*,R*)]-2-hydroxy-4-oxo-3-methoxy-4-[(phenylmethoxy)-amino]-butanoate and ethyl[2R-(R*,R*)]-2-methoxy-4-oxo-3-hydroxy-4-[(phenylmethoxy)-amino]-butanoate were dissolved in 5 ml of pyridine and 2 ml of methylene chloride and at −10° C., 457 mg of tosyl chloride were added. After standing over night at −10° C., the mixture was poured into iced water containing 5.2 ml of concentrated hydrochloric acid. After extraction with methylene chloride and chromatography over silica (eluent:ethyl acetate-hexane 1:1), 110 mg of starting product, 430 mg of ethyl[2R-(R*,R*)]2-[4-(methylphenylsulfonyl)-oxy]-4-oxo-3-methoxy-4-[(phenylmethoxy)-amino]-butanoate and 90 mg of ethyl[2R-(R*,R*)]-3-[4-methylphenylsulfonyl)-oxy]-4-oxo-2-methoxy-4-[(phenylmethoxy)-amino]-butanoate were obtained.

The expected product after crystallization from a methylene chloride-hexane mixture (8-2) melted at 101°–102° C. and had a specific rotation of $[\alpha]_D^{25}$=+12° (c=1.03% in CHCl$_3$).

Analysis: C$_{21}$H$_{25}$O$_8$NS: Calculated: %C 55.86 %H 5.58 %N 3.10 %S 7.1. Found: 55.62 5.49 3.13 6.8.

NMR $^1$H (60 MHz): 1.25 ppm (t, 3H); 2.34 (s, 3H); 3.3 (s, 3H); 4.2 (q, 2H); 4.30 (d, J=3 Hz, 1H); 4.68 (d, 2H); 5.35 (d, J=3 Hz, 1H); 7.1–7.3 (7H); 7.7 (d, 2H); 8.8 (1H).

Step B''

Ethyl(2-S,-trans)-1-benzyloxy-3-methoxy-4-oxo-2-azetidine-carboxylate 245 mg of the product of Step B' in solution in 3 ml of acetone were added to a suspension of 223 mg of potassium carbonate in acetone at 60° C. After 1 hour, the reaction mixture was filtered and evaporated to dryness to obtain ethyl(2-S,-trans)-1-benzyloxy-3-methoxy-4-oxo-2-azetidine-carboxylate quantitatively with a specific rotation of $[\alpha]_D^{25}$=+37° (c=1.6% in CHCl$_3$).

Analysis: C$_{14}$H$_{17}$O$_5$N: Calculated: %C 60.20 %H 6.13 %N 5.01. Found: 60.05 6.21 5.05.

NMR $^1$H (60 MHz): 1.3 ppm (t, 3H); 3.4 (s, 3H); 4 (d, 1H, J$_{3,4}$=1.5 Hz); 4.2 (q, 2H); 4.3 (d, 1H, J$_{3,4}$=1.5 Hz); 4.98 (s, 2H); 7.25 (s, 5H).

EXAMPLE 4

Ethyl(2S-trans)-1,3-bis-benzylozy-4-oxo-2-azetidine-carboxylate

Step A

Ethyl[2R-(R*,R*)]2-hydroxy-4-oxo-3-benzyloxy-4-[(benzyloxy)-amino]-butanoate 380 mg of diethyl[R-(R*,R*)]-2-hydroxy-3-benzyloxy butanedioate were reacted by the procedure of Step A of Example 1 with 430 mg of potassium carbonate and the crude product obtained was reacted for half an hour with 624 mg of O-benzyl-hydroxylamino hydrochloride and 750 mg of ethyl-1-dimethylaminopropyl-3-3-carbodiimide hydrochloride. After extraction and chromatography, 180 mg of starting product, 70 mg of [2R-(R*,R*)]-2-hydroxy-N,N'-3-tris benzyloxy-butanediamide and 290 mg of a mixture of [2R-(R*,R*)]-2-hydroxy-4-oxo-3-benzyloxy-4-[(phenylmethoxy)-amino]-butanoate and ethyl[2R-(R*,R*)]-3-hydroxy-4-oxo-2-phenylmethoxy-4-[(benzyloxy)-amino]-butanoate were obtained.

Physico-chemical analysis of ethyl[2R-(R*,R*)]2-hydroxy-4-oxo-3-benzyloxy-4-[(benzyloxy)-amino]-butanoate.

NMR $^1$H (60 MHz): 1.2 ppm (2t, 3H); 3.75–3.86 (strong, 9H); 7.18 (10H); 9.13 and 9.33 (1H, 7/3).

Step B'

Ethyl[2R-(R*,R*)]-2[(4-methylphenylsulfonyl)-oxy]-4-oxo-3-(benzyloxy)-4-[(benzyloxy)-amino]-butanoate 560 mg of the mixture of ethyl[2R-(R*,R*)]-2-hydroxy-4-oxo-3-benzyloxy-4-[(benzyloxy)-amino]-butanoate and ethyl(2R-(R*,R*)]-3-hydroxy-4-oxo-2-benzyloxy-4-[(benzyloxy)-amino]-butanoate were dissolved in 3 ml of pyridine and 2 ml of methylene chloride at −10° C. 710 mg of tosyl chloride were added and the mxiture stood for 3 days at −10° C. and then was poured into ice containing 3.1 ml of 12N hydrochloric acid. After extraction and chromatography (ethyl acetate-hexane 1:1), 100 mg of starting product, 390 mg of ethyl[2R-(R*,R*)-2-[(4-methylphenylsulfonyl)-oxy]-4-oxo-3-(benzyloxy)-4-[(benzyloxy)-amino]-butanoate and 10 mg of ethyl[2R-(R*,R*)]-3-[(4-methylphenylsulfonyl)-oxy]-4-oxo-2-(phenylmethoxy)-4-[(phenylmethoxy)-amino]-butanoate were obtained.

The desired product after crystallization from a mixture of methylene chloride-hexane (7/3) melted at 83°–84° C. and had a specific rotation of $[\alpha]_D^{25} = +20°$ (c=0.87% in CHCl$_3$).

Analysis: C$_{27}$H$_{29}$O$_8$NS: Calculated: %C 61.46 %H 5.54 %N 2.65 %S 6.1. Found: 61.24 5.38 2.62 5.8.

NMR $^1$H (60 MHz): 1.15 ppm (t, 3H); 2.3 (s, 3H); 4 (qd, 2H); 4.35 (s, 2H); 4.4 (d, 1H, J=2.5 Hz); 4.58 (s, 2H); 5.25 (d, 1H, J=2.5 Hz); 7.05–7.25 (12H); 7.6 (d, 2H); 8.77 (s widened, 1H).

Step B''

Ethyl(2S-trans)-1,3-bis-(benzyloxy)-4-oxo-2-acetidine-carboxylate 290 mg or 0.55 mM of the compound of Step B' dissolved in 5 ml of acetone was added to a suspension of 3 equiv. (228 mg) of potassium carbonate in 5 ml of acetone at 60° C. After 1 hour of stirring, followed by filtering and evaporating the solvent to dryness, 156 mg (yield=80%) of ethyl(2S-trans)-1,3-bis-(benzyloxy)-4-oxo-2-azetidine-carboxylate were isolated by chromatography. It had a specific rotation of $[\alpha]_D^{25} = +40°$ (c=0.63% in CHCl$_3$).

Analysis: C$_{20}$H$_{21}$O$_5$N: Calculated: %C 67.59 %H 5.96 %N 3.94. Found: 67.33 5.93 3.88.

NMR $^1$H (80 MHz, CDCl$_3$): 1.6 ppm (t, 3H); 4.01 (d, 1H, J$_{3,4}$=1.5Hz); 4.23 (q, 2H); 4.55 (d, 1H, J$_{3,4}$=1.5 Hz); 4.68 (s, 2H); 5.1 (s, 2H); 7.4–7.6 (10H).

EXAMPLE 5

Methyl(2S-trans)-1-hydroxy-4-oxo-3-phenylmethoxy-2-azetidine-carboxylate 170 mg of azetidinone of Example 2 were dissolved in 10 ml of ethyl acetate and hydrogenated in the presence of 170 mg of 5% palladium on carbon for an hour under 3 bars of pressure. The catalyst was then filtered and after evaporation and chromatography, 100 mg of methyl(2S-trans)-1-hydroxy-4-oxo-3-phenylmethoxy-2-azetidine-carboxylate were obtained.

NMR $^1$H (60MHz, CDCl$_3$): 3.7 (s, 3H); 4.28 (d widened, 1H, J$_{3,4}$=1.5 Hz); 4.55 (d, widened 1H, J$_{3,4}$=1.5 Hz); 4.55 (d widened 1H J$_{3,4}$=1.5 Hz); 4.62 (s, 2H); 7.2 (s, 5H).

EXAMPLE 6

Ethyl(2S-trans)-1-hydroxy-4-oxo-3-benzyloxy-2-azetidine-carboxylate 115 mg of 5% palladium on carbon were added to a solution of 115 mg of azetidinone of Example 4 in 10 ml of ethyl acetate. After 1 hour of hydrogenation under 3 bars, the catalyst was filtered off and the filtrate was evaporated. By chromatography, 61 mg (Yield=77%) of ethyl(2S-trans)-1-hydroxy-4-oxo-3-benzyloxy-2-azetidine-carboxylate were obtained.

NMR $^1$H (200 MHz, CDCl$_3$): 1.9 (td, 3H); 4.22 (qd, 2H); 4.29 (d, 1H, J$_{3,4}$=1.22 Hz); 4.52 (d, 1H, J$_{3,4}$=1.22 Hz); 4.70 (q, 2H); 7.59 (s, 5H).

EXAMPLE 7

Ethyl(2S-trans)-4-oxo-3-methoxy-2-azetidine-carboxylate

A solution of 270 mg of azetidinone of Example 3 in 25 ml of ethyl acetate was reduced with hydrogen in the presence of 270 mg of 5% palladium on carbon at 3 bars for an hour. The catalyst was filtered off and the filtrate was evaporated. The residue was dissolved in 5 ml of methanol and added under argon to 30 ml of an aqueous solution of 2.35 g of sodium bicarbonate and 4 ml of an aqueous solution of (771 mg) 20% titanium chloride. The pH was adjusted to 6.5 with an aqueous solution of 10% sodium carbonate. After stirring for an hour, the mixture was extracted with ethyl acetate and after chromatography (eluent:ethyl acetate/hexane 2:8), 50 mg of ethyl (2S-trans)-4-oxo-3-methoxy-2-azetidine-carboxylate having a specific rotation of $[\alpha]_D^{25} = +15°$ (c=1.3% in CHCl$_3$) were obtained.

Analysis: C$_7$H$_{11}$O$_4$N: Calculated: %C 48.55 %H 6.40 %N 8.09. Found: 48.01 6.39 7.88.

IR: COOR=1740; lactam=1795.

NMR $^1$H (200 MHz, CDCl$_3$): 1.32 (t, 3H); 3.55 (s, 3H); 4.15 (d, 1H, J$_{3,4}$=2 Hz); 4.27 (q, 2H); 4.63 (t, 1H, J$_{3,4}$=J$_{3,1}$=2 Hz); 6.49 (s widened, 1H).

EXAMPLE 8

Methyl(2S-trans)-1,3-bis-(benzyloxy)-4-oxo-2-azetidine-carboxylate

Step A 1-methyl ester of [(2-S-(R*,R*)]-2-hydroxy-3-benzyloxy-butane-dioic acid 200 units of pork liver esterase (PLE) were added with stirring to a solution of 560 mg of dimethyl[R-(R*,R*)]-2-hydroxy-3-phenylmethoxy butanedioate in 3.3 ml of phosphate buffer (0.1M, pH8). The pH was held at 8 by addition of a 1N sodium hydroxide and after 8 hours of reaction, the starting product was extracted with ether (30%). The aqueous phase was acidified with Amberlite ® IRN 77 (H+) and after filtering and extraction with ethyl acetate, 240 mg of 1-methyl ester of [(2-S-(R*,R*)]-2-hydroxy-3-benzyloxy-butanedioic acid containing about 10% of starting product were obtained by evaporation.

Step B

Methyl[2R-(R*,R*)]-2-hydroxy-4-oxo-3-benzyloxy-4-[(benzyloxy-amino)-butanoate

The mixture of Step A was dissolved in 5 ml of aqueous tetrahydrofuran containing 150 mg of O-benzylhydroxylamine hydrochloride and 300 mg of ethyl-1-dimethylaminopropyl-3,3-carbodiimide hydrochloride. After half an hour of reaction, the mixture was extracted with methylene chloride to obtain a mixture of methyl[2R-(R*,R*)]-2-hydroxy-4-oxo-3-benzyloxy-4-[(benzyloxy-amino]-butanoate (90%) and the starting product of Step A (10%).

Step C

Methyl[2R-(R*,R*)]-2-[(4-methylphenylsulfonyl)-oxy]-4-oxo-3-benzyloxy-4-[benzyloxy-amino]-butanoate Using the procedure of Step B3' of Example 2, 400 mg of tosyl chloride in 5 ml of pyridine and methylene chloride at −10° C. were reacted with the product of Step B to obtain 720 mg of mixture is obtained. After chromatography 200 mg of methyl[2R-(R*,R*)]-2-[(4-methylphenylsulfonyl)-oxy]-4-oxo-3-benzyloxy-4-[benzyloxy-amino]-butanoate are obtained.

Step D

Ethyl(2S-trans)-1,3-bis-benzyloxy-4-oxo-2-acetidine-carboxylate

Using the procedure of Step B3" of Example 2, the product of Step C was reacted to obtain ethyl(2S-trans)-1,3-bis-benzyloxy-4-oxo-2-azetidine-carboxylate which was identical to that obtained at Step 2.

EXAMPLE 9

Ethyl(2S,cis)1-acetoxy-4-oxo-3-//benzyloxycarboxyl-/amino/2-azetidine-carboxylate

Step A

Ethyl(2S-trans)-1-acetoxy-4-oxo-3-benzyloxy-2-azetidine-carboxylate 150 mg of ethyl(2S-trans)-1-hydroxy-4-oxo-3-benzyloxy-2-azetidine-carboxylate of Example 6 were dissolved in 8 ml of anhydrous methylene chloride and 0.07 ml of acetic anhydride and 0.012 ml of triethylamine were added. After 2 hours of reaction and extraction with methylene chloride, 200 mg of a mixture was obtained and 136 mg of ethyl(2S-trans)-1-acetoxy-4-oxo-3-benzyloxy-2-azetidine-carboxylate were isolated by chromatography. It had a specific rotation of $[\alpha]_D^{25} = +9.5°$ (c=3.31% in CHCl$_3$).

Analysis: $C_{15}H_{17}O_6N$: Calculated: %C 58.62 %H 5.58 %N 4.56. Found: 58.45 5.74 4.84.

NMR $^1$H (80 MHz; CDCl$_3$): 1.27 (t, 3H); 2.16 (s, 3H); 4.22 (q, 2H); 4.5 (d, 1H, J$_{3,4}$=2 Hz); 4.77 (s widened, 3H); 7.35 (s, 5H).

Step B

Ethyl(2S-trans)-1-acetoxy-4-oxo-3/(trifluoromethylsulfonyl)oxy/2-azetidine-carboxylate A solution of 128 mg of the product of Step A in 15 ml of ethyl acetate in the presence of 128 mg of 10% palladium on active carbon was hydrogenated under 3 bars pressure for 90 minutes. The catalyst was filtered off and the solvent was evaporated. The residue was taken up in 6 ml of methylene chloride and 0.1 ml of pyridine and 0.08 ml of trifluoromethylsulfonic anhydride were added at 0° C. After half an hour of reaction, the reaction mixture was poured into an iced solution of ammonium chloride and extracted with methylene chloride to obtain 60 mg of ethyl(2S-trans)-1-acetoxy-4-oxo-3/(trifluoromethylsulfonyl)oxy/2-azetidine-carboxylate NMR $^1$H (80 MHz; CDCl$_3$): 1.32 (t, 3H); 2.2 (s, 3H); 4.32 (q, 2H); 4.7 (d, 1H, J=2Hz); 5.7 (d, 1H, J=2 Hz).

Step C

Ethyl(2S-cis)-1-acetoxy-4-oxo-3-/(benzyloxy)carbonyl-/amino/2-azetidine-carboxylate A solution of 60 mg of the product of Step B in 8 ml of benzene was mixed with 30 mg of sodium azide and 5% tricaprylmethylammonium chloride at 60° C. After 1 hour of reaction, the mixture was extracted with methylene chloride and the solvent was evaporated. The residue was dissolved in 8 ml of ethyl acetate and hydrogenated under 3 bars in the presence of 100 mg of 10% palladium on active carbon. After 2 hours, the catalyst was filtered off, and the solvent was evaporated. The residue was dissolved in 4 ml of an acetone-water mixture (1-1) and 0.024 ml of benzyl chloroformate and 28 mg of sodium bicarbonate were added thereto. After 1 hour of reaction, the mixture was evaporated to dryness and the residue was taken up in methylene chloride. The residue was chromatographed to obtain 20 mg of ethyl(2S-cis)-1-acetoxy-4-oxo-3-N-benzyloxycarbonylamino-2-azetidine-carboxylate.

PREPARATIONS OF STARTING MATERIALS

Preparation 1

Dimethyl[R-(R*,R*)]-2-hydroxy-3-methoxy-butanedioate 450 mg of dimethyl[R-(R*,R*)]-2,3-dihydroxy-butanedioate and 50 mg of anhydrous stannous chloride were dissolved in 10 ml of acetonitrile, and a solution of diazomethane in ether was added at 0° C. until the solution stayed yellow. The solvents were evaporated under vacuum and the residue was chromatographed over a short column of silica gel (eluent:ethyl acetate/hexane. ½). The product was distilled to obtain 292 mg of dimethyl[R-(R*,R*)]-2-hydroxy-3-methoxy-butanedioate with a boiling point of 35° C. at 0.4 mm Hg and having a specific rotation of $[\alpha]_D^{25} = +32°$ (c=1.14% in CHCl$_3$).

Analysis: C$_7$H$_{12}$O$_6$: Calculated: %C 43.75 %H 6.29. Found: 43.63 6.38.

Preparation 2

Dimethyl[R-(R*,R*]-2-hydroxy-3-benzyloxy-butanedioate 3 g of dimethyl(4-R-trans)-2-methyl-2-phenyl-1,3-dioxolane-4,5-dicarboxylate and 3 g of sodium cyanoborohydride were dissolved in 35 ml of acetonitrile and a saturated solution of HCl in ether was added dropwise with stirring until the pH reached 2. After 2 hours at ambient temperature, the mixture was poured into a saturated aqueous solution of sodium bicarbonate and was extracted with CH$_2$Cl$_2$. The organic phase was washed with water, dried and evaporated. The residue was chromatographed over a short column of silica and crystallized from cyclohexane to obtain 255 g of pure dimethyl[R-(R*,R*)]-2-hydroxy-3-benzyloxybutanedioate melting at 69° C. and having a specific rotation of $[\alpha]_D^{25} = +87°$ (c=0.98% in CHCl$_3$).

Analysis: C$_{13}$H$_{16}$O$_6$: Calculated: %C 58.20 %H 6.01. Found: 58.27 6.03.

Preparation 2'

Dimethyl[R-(R*,R*)]-2-hydroxy-3-benzyloxy-butanedioate 3 g of dimethyl[R-R*,R*,)]-2,3-dihydroxy-butanedioate were dissolved in 30 ml of anhydrous tetrahydrofuran under argon and 13.6 ml of a 2.5N solution of sodium hexamethyldisilazide in toluene was added thereto, followed after 10 minutes by 2.4 ml of benzyl bromide. The mixture was stirred for 5 hours and then was poured on ice and extracted with CH$_2$Cl$_2$. The organic phase was washed with water, dried and evaporated. The residue was chromatographed over a column of silica gel and the first eluted product was 1.82 g of dimethyl[R-(R*,R*)]-2,3-bis-(phenylmethoxy)-butanedioate and then 1.35 g of dimethyl[R-(R*,R*)]-2-hydroxy-3-benzyloxy-butanedioate identical to the product of preparation 2.

Preparation 3

Diethyl[R-(R*,R*)]-2,3-dihydroxy-butanedioate 1.50 g of diethyl[R-(R*,R*)]-2,3-dihydroxy-butanedioate and 100 mg of anhydrous stannous chloride were dissolved in 30 ml of acetonitrile and at 0° C., a solution of diazomethane in ether was added until the solution stayed yellow. The solvents were evaporated under vacuum and the residue was purified by chromatography over a column of silica gel (eluent:ethyl acetate/hexane, ⅓). The product was distilled to obtain 1.2 g of diethyl[R-(R*,R*)]-2,3-dihydroxy-butanedioate with a boiling point of 115° C. at 0.5 mm Hg and a specific rotation of $[\alpha]_D^{25} = +37°$ (c=1.09 in CHCl$_3$).

Analysis: C$_9$H$_{16}$O$_6$: Calculated: %C 49.09 %H 7.32. Found: 48.82 7.27.

Preparation 4

Diethyl[R-(R*,R*)]-2-hydroxy-3-benzyloxy-butanedioate 3 g of diethyl(4R-trans)-2-methyl-2-phenyl-1,3-dioxolane-4,5-dicarboxylate and 3 g of sodium cyanoborohydride were dissolved in 35 ml of acetonitrile and a saturated solution of HCl in ether was added dropwise to adjust the pH to 2. After 2 hours of stirring at room temperature, the mixture was extracted with CH$_2$Cl$_2$. After evaporation of the solvents under vacuum, the residue was chromatographed over a column of silica gel to obtain 2.24 g of diethyl[R-(R*,R*)]-2-hydroxy-benzyloxy-butanedioate in the form of an oil having a specific rotation of $[\alpha]_D^{25} = +73°$ (c=1.35% in CHCl$_3$).

Analysis: C$_{15}$H$_{20}$O$_6$: Calculated: %C 60.80 %H 6.80. Found: 60.70 6.80.

Various modifications of the products and processes of the invention may be made without departing from the spirit or scope thereof and it should be understood that the invention is intended to be limited only defined in the appended claims.

What is claimed is:

1. A 2-azetidinone of the formula

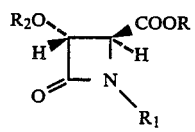

wherein R is alkyl of 1 to 4 carbon atoms, R$_1$ is selected from the group consisting of hydrogen, —OH, protected hydroxy and —OCH$_2$—COOR', R' is selected from the group consisting of hydrogen and alkyl of 1 to 4 carbon atoms and R$_2$ is a hydroxyl protective group.

2. A compound of claim 1 wherein R$_2$ is benzyl and R$_1$ is hydrogen.

3. A compound of claim 1 wherein R$_2$ is alkyl of 1 to 4 carbon atoms.

* * * * *